US00PP17250P2

(12) United States Plant Patent
Giesen

(10) Patent No.: US PP17,250 P2
(45) Date of Patent: Nov. 28, 2006

(54) ***LOBELIA* PLANT NAMED 'LOB BULE'**

(50) Latin Name: *Lobelia erinus*
Varietal Denomination: Lob Bule

(75) Inventor: Eric Giesen, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/206,285

(22) Filed: Aug. 18, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Jondle & Associates P.C.

(57) ABSTRACT

A new *Lobelia* plant particularly distinguished by its compact, mounded, and pendant plant habit, short internodes, and large flower size with a very intense cobalt blue color is disclosed.

1 Drawing Sheet

Genus and species: *Lobelia erinus.*
Variety denomination: 'Lob Bule'.

BACKGROUND OF THE NEW PLANT

The present invention comprises a new and distinct cultivar of *lobelia*, botanically known as *Lobelia erinus*, and hereinafter referred to by the cultivar name 'Lob Bule'. The new cultivar originated from a hybridization made in 2002 in Andijk, The Netherlands. The female parent was 'LOB02-12-1', a white proprietary *lobelia* line (unpatented), while the male parent was 'LOB02-14-1', a blue proprietary *lobelia* line (unpatented).

The new cultivar was created in 2002 in Andijk, The Netherlands and has been asexually reproduced repeatedly by vegetative cuttings and tissue culture in Gilroy, Calif., and Andijk, The Netherlands over a two-year period. The plant has also been trialed at Gilroy, Calif., and Andijk, The Netherlands. The present invention has been found to be stable and true to type and to retain its distinctive characteristics through successive asexual propagations.

SUMMARY OF THE INVENTION

The following are the most outstanding and distinguishing characteristics of this new cultivar when grown under normal horticultural practices in Gilroy, Calif., and Andijk, The Netherlands.

1. A compact, mounded, and pendant plant habit;
2. Short internodes; and
3. A large flower size with a very intense cobalt blue color.

DESCRIPTION OF PHOTOGRAPH

This new *lobelia* plant is illustrated by the accompanying photograph which shows overall plant habit including blooms, buds, and foliage of the plant in full color; the colors shown are as true as can be reasonably obtained by conventional photographic procedures. The photograph is of a 4½-month-old plant grown in a six-inch pot in a greenhouse with natural light in a late winter/spring trial setting.

The accompanying photograph shows the overall plant habit including blooms, buds, and mature foliage; the inset shows mature inflorescences.

DESCRIPTION OF THE NEW CULTIVAR

The following detailed descriptions set forth the distinctive characteristics of 'Lob Bule'. The data which define these characteristics were collected from asexual reproductions carried out in Gilroy, Calif. The plant history was taken on six-month-old plants grown in one-gallon pots in a poly-covered greenhouse. Color readings were taken in the greenhouse in the summer season under natural light. Color references are primarily to The R.H.S. Colour Chart of The Royal Horticultural Society of London (R.H.S.) (2001 edition). Texture description details were observed under a dissecting microscope.

DETAILED BOTANICAL DESCRIPTION

Classification:
- *Botanical.*—*Lobelia erinus.*
- *Common name.*—*Lobelia.*

Parentage:
- *Female parent.*—'LOB02-12-1' proprietary *lobelia* line (unpatented).
- *Male parent.*—'LOB02-14-1' proprietary *lobelia* line (unpatented).

Growth:
- *Growth and branching habit.*—Vigorous growth habit; dense and freely branched with short internodes.
- *Form.*—Low mounding and pendulous.
- *Height.*—20–24 cm, from top of soil, including flowers.
- *Width.*—30–40 cm, including flowers.
- *Time to produce a finished flowering plant.*—9–11 weeks for a 6-inch pot.
- *Outdoor plant performance.*—Used as patio planters, in mixed container plantings, or in garden beds.
- *Time to initiate roots.*—21–28 days at 68° F.–74° F.
- *Root description.*—Fibrous, freely-branching, and white.

Leaves:
- *Arrangement.*—Alternate.
- *Mature leaf.*—Color: Upper surface: RHS 138A, but darker. Lower surface: RHS 138B. Length (fully expanded): 4.9–5.1 cm. Width (fully expanded): 1.8–2.0 cm. Shape: Broadly ovate to elliptical. Margin: Dentate. Apex: Acute. Base: Attenuate to cuneate. Texture: Glabrous. Venation: Palmate. Venation color (upper surface): RHS 144B. Venation color (lower surface): RHS 137C.

*Petioles.*—Length: 0.1–0.2 cm. Width: 0.2 cm. Color: RHS 144B. Texture: Glabrous.

Stems:

*Length.*—10–20 cm.

*Diameter.*—0.15 cm.

*Internode length.*—0.5–0.7 cm.

*Color.*—RHS 144A.

*Texture.*—Glabrous.

*Stem anthocyanin.*—Absent.

*Peduncle.*—Color: RHS 137A. Length: 6.0–15.0 cm. Diameter: 0.15 cm. Texture: Glabrous.

Flower buds:

*Shape.*—Spathulate.

*Diameter.*—0.4 cm.

*Length.*—0.8–1.0 cm.

*Color when bud is first starting to open.*—RHS N187C with a hint of blue.

Inflorescence:

*Blooming habit.*—Continuous throughout the growing season from spring to the fall.

*Lastingness of individual blooms on plant.*—4–8 days depending on weather conditions.

*Fragrance.*—None.

*Average number of flowers and buds per lateral branch (12 cm pots, in full flower and branches approximately 25 cm in length).*—15–30 open flowers and 20–35 buds.

*Inflorescence type.*—Flowers form at apical axils, with one flower per axil; flowers are labiate; upper petal has two small lobes and lower lip has three larger and broader lobes; lobes are fused at the base.

Flowers:

*Flower diameter.*—1.9–2.2 cm.

*Flower height.*—1.7–1.8 cm.

*Upper lobes.*—Color: Upper surface: RHS 96B, but slightly lighter. Lower surface: RHS 97A. Length: 0.7 cm. Width: 0.2 cm at the widest part. Shape: Elliptical. Apex: Mucronulate. Margin: Entire. Texture: Papillose.

*Lower lobes.*—Color: Upper surface: RHS 96B with small basal spots of RHS N155A (but whiter) and RHS 96A. Lower surface: RHS 97A, but slightly lighter. Length: 1.0–1.2 cm. Width: 0.7 cm. Shape: Obovate. Apex: Murconulate. Margin: Entire. Texture: Glabrous.

*Flower throat.*—Color: RHS N155A with spots of RHS N88A and RHS N88B in different shades and two greenish lines of RHS N144C. Texture: Glabrous and whiskered.

*Corolla.*—Tube color outside: RHS 97A but lighter. Tube length: 1.0 cm. Diameter: 0.4–0.5 cm at the widest part.

*Sepals.*—Color (both upper and lower surfaces): RHS 137A. Apex: Acute. Base: Cuncate. Margin: Entire. Shape: Linear. Texture: Glabrous. Length: 0.6–0.7 cm. Width: 0.05–0.1 cm.

Reproductive organs:

*Androecium.*—Number of anthers: 5. Pollen color: RHS N200A. Pollen amount: Scarce.

*Gynoecium.*—Pistil number per flower: 1. Pistil length: 1.1 cm. Stigma color: RHS 86A. Style color: RHS 144C. Style length: 0.8 cm. Ovary color: Closest to RHS N189A.

Fruit and seed set: Has not been observed.

Disease and insect resistance: Has not been observed.

COMPARISON WITH KNOWN CULTIVARS

'Lob Bule' differs from the female parent, 'LOB02-12-1', proprietary breeding line (unpatented), in that 'Lob Bule' has blue flowers while 'LOB02-12-1' has white flowers. Additionally, 'Lob Bule' has a more compact plant habit, better branching, and flowers earlier than 'LOB02-12-1'.

'Lob Bule' differs from the male parent, 'LOB02-14-1', proprietary breeding line (unpatented), in that 'Lob Bule' has a more compact plant habit, better branching, larger leaves, and flowers earlier than 'LOB02-14-1'.

'Lob Bule' differs from the commercial variety 'Laguna Blue Ice' (U.S. Plant Pat. No. 12,947) in that 'Lob Bule' has a trailing (compact, bushy, and pendulous) plant habit, while 'Laguna Blue Ice' has a mounding plant habit. 'Lob Bule' has long small leaves, while 'Laguna Blue Ice' has larger, rounder, and broader leaves. Additionally, 'Lob Bule' has intense blue flowers, while 'Laguna Blue Ice' has less intense blue flowers with a very large white eye (or white center).

I claim:

1. A new and distinct *Lobelia* plant, named 'Lob Bule', as shown and described herein.

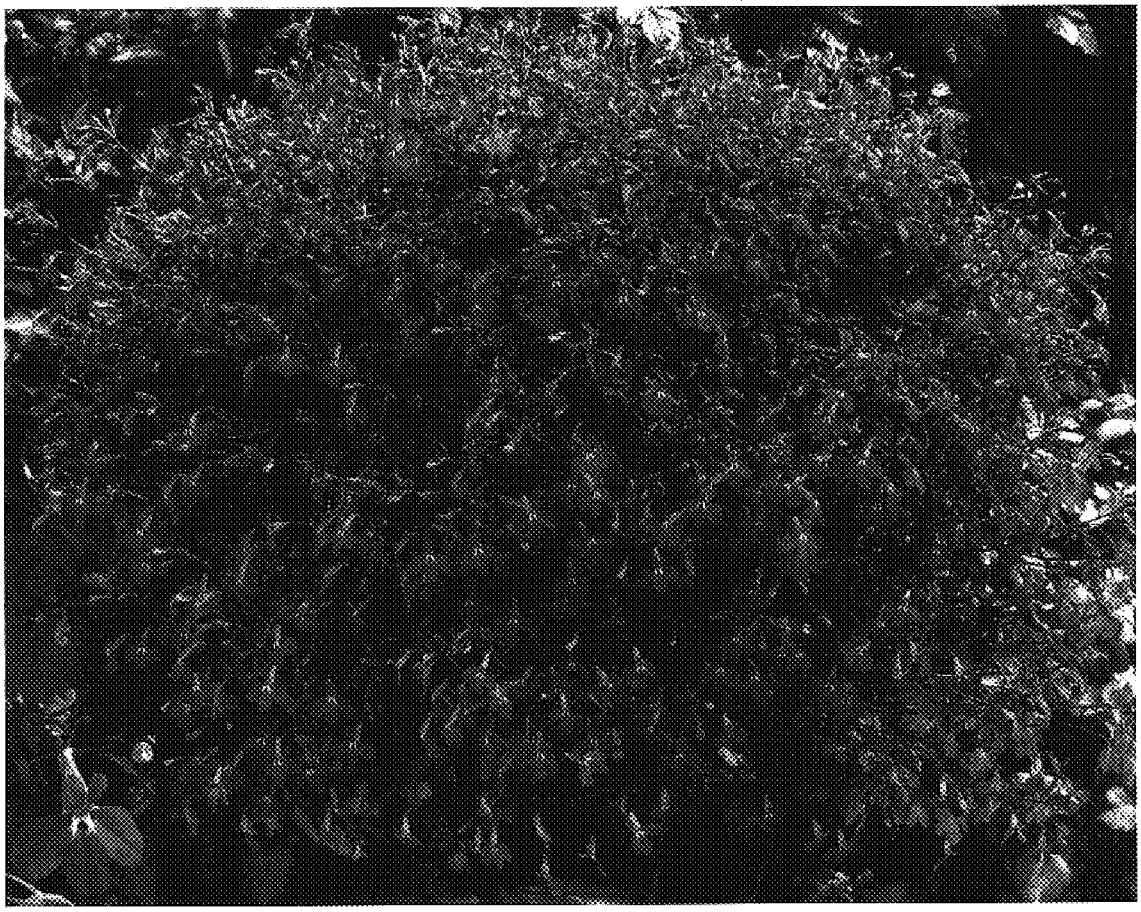

* * * * *